United States Patent [19]

Scantlebury et al.

[11] Patent Number: 4,531,916
[45] Date of Patent: Jul. 30, 1985

[54] DENTAL IMPLANT WITH EXPANDED PTFE GINGIVAL INTERFACE

[75] Inventors: Todd V. Scantlebury; Jeanne B. Ambruster; Carl W. Bolton, all of Flagstaff; Stephen E. Campbell, Cave Creek; La Thaggar Green, III, Flagstaff, all of Ariz.

[73] Assignee: W. L. Gore & Associates, Inc., Newark, Del.

[21] Appl. No.: 511,995

[22] Filed: Jul. 8, 1983

[51] Int. Cl.³ .................................................. A61C 8/00
[52] U.S. Cl. ..................................... 433/173; 433/176
[58] Field of Search ................. 433/201, 173, 174; 128/1 R

[56] References Cited

U.S. PATENT DOCUMENTS

| | | | |
|---|---|---|---|
| 3,849,887 | 12/1974 | Brainin | 32/10 A |
| 3,934,347 | 1/1976 | Lash et al. | 32/10 A |
| 3,953,566 | 4/1976 | Gore | 264/288 |
| 3,977,081 | 8/1976 | Zambelli | 32/10 A |
| 4,178,686 | 12/1979 | Riess | 433/201 |
| 4,187,390 | 2/1980 | Gore | 174/102 |
| 4,244,689 | 1/1981 | Ashman et al. | 433/175 |
| 4,270,905 | 6/1981 | Mohammed | 433/173 |
| 4,302,188 | 11/1981 | Driskov | 433/173 |
| 4,321,914 | 3/1982 | Begouac et al. | 128/1 R |
| 4,359,318 | 11/1982 | Gittleman | 433/173 |

OTHER PUBLICATIONS

Peterson et al., "Clinical, Radiographical, and Histological Evaluation of Porous Rooted Polymethylmethacrylate Dental Implants" J. Dent. Res. Jan., 1979.
Hottel et al. "The Effect of Change of Surface Microstructure of Carbon Oral Implants on Gingival Structures" J. Oral Maxillofac. Surg. 40:647-650 (1982).
Kent et al., "Proplast in Dental Facial Reconstruction" Oral Surg. 39:347-355 Mar., 1975.
Kent et al. "Pilot Studies of a Porous Implant in Dental and Oral Surgery" J. Oral Surg. 30:608-615 (1972).
Homsy et al. "Material for Oral Implantation–Biological and Functional Criteria J.A.D.A. 86:817-832 (1973).

Primary Examiner—Robert Peshock
Attorney, Agent, or Firm—Finnegan, Henderson, Farabow, Garrett & Dunner

[57] ABSTRACT

A dental implant device. A dental implant device having: (a) a root structure made of a biocompatible, mechanically suitable prosthetic material; (b) a cervical segment projecting above the root structure, made of a biocompatible, nonporous material and having smooth surfaces and together with the root structure forming a member; and (c) a gingival interface made of expanded polytetrafluoroethylene having a porous structure for the ingrowth of connective tissue, located adjacent to the juncture of the root structure and the cervical segment attached to the member and forming a border around the apical end of the cervical segment. The expanded polytetrafluoroethylene provides for an interlocking between the gingival tissue and the pergingival portion of the dental implant preventing bacterial penetration and infection where the implant extends into the oral cavity.

24 Claims, 7 Drawing Figures

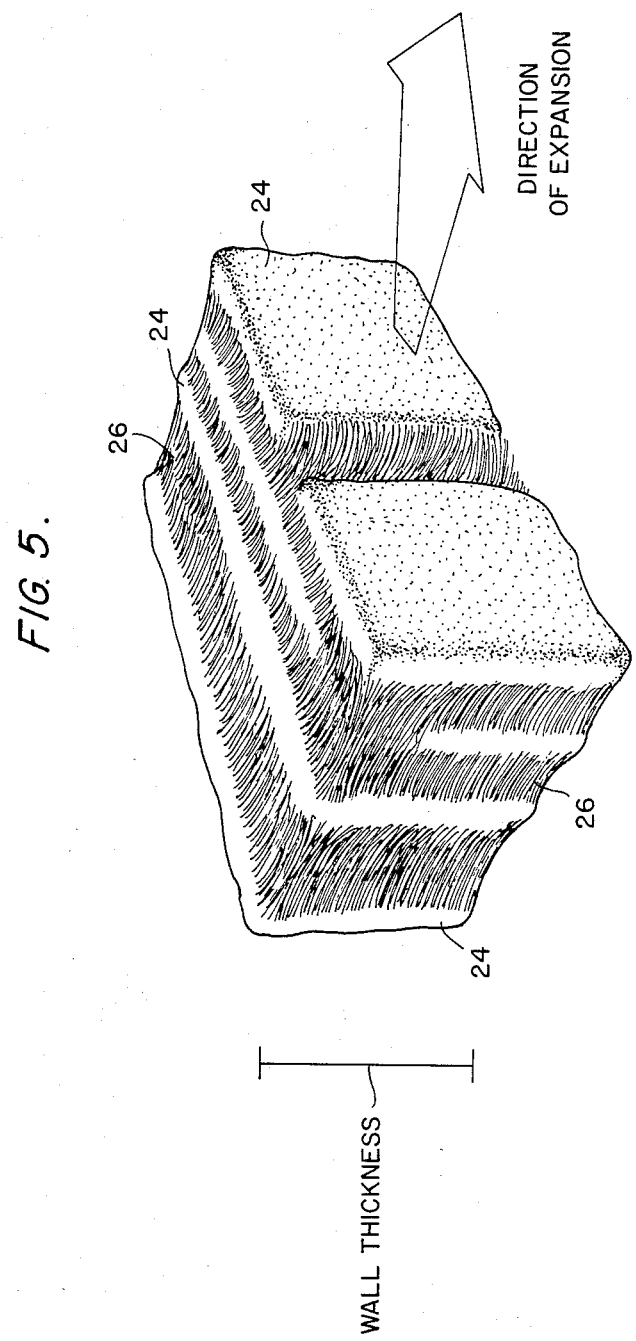

DENTAL IMPLANT WITH EXPANDED PTFE GINGIVAL INTERFACE

BACKGROUND OF THE INVENTION

The present invention relates to a dental implant, in particular to an implant with an improved gingival interface which prevents bacterial penetration where the implant extends into the oral cavity.

Over the past forty years the dental community has attempted to develop subperiosteal and endosseous dental implants which could be considered successful and effective. The 1978 NIH-Harvard Consensus Development Conference recommended that only those implants which provide functional service for five years in 75 percent of the cases be considered successful (Schnitman, P. A. and Schulman, L. B., eds.; *Dental Implants Benefit and Risk,* Department of Health and Human Resources, 1980, p. 329). The American Dental Association indicates that as many as 60 percent of the currently used endosseous and unilateral subperiosteal implants have failed after only two years or less (American Dental Association, *Dentist's Desk Reference: Materials, Instruments and Equipment,* 1981, p. 149).

Subperiosteal implants rest on the jaw bone and endosseous implants lie in the jaw bone. The portion of these implants which is positioned beneath the gum tissue (gingival tissue) in or on the jaw bone is the root portion. Both the subperiosteal and endosseous implant extend through the gum tissue into the mouth and serve to support artificial teeth and other dental devices. Endosseous and subperiosteal implants are made of metallic, ceramic, or polymeric materials. Because the implants serve as structures for artificial teeth, they are generally implanted in toothless areas of the mouth.

Dental implants must be made of mechanically suitable and biocompatible materials. Biocompatible materials do not corrode in the oral environment or adversely affect either the soft or bony tissue of the mouth. Mechanically suitable materials withstand the normal forces of chewing without bending, fracturing, or otherwise becoming mechanically compromised. Suitable materials which have been previously developed include: metals, such as cobalt chromium alloys, stainless steels, and titanium or titanium alloys; ceramics, such as aluminum oxide or hydroxylapatite; and several polymers and carbon compositions.

Through time, implantation techniques and endosseous implant designs have been refined. Early trials revealed that implants had to be inserted firmly in sufficient volumes of mandibular or maxillary bone. Implants placed loosely in a bone socket became surrounded by fibrous tissue and through progressive movement failed. Thick or large diameter implants placed in thin, bony ridges were not supported by sufficient volumes of bone. Implants with sharp edges or undercuts in the root portion produced stress concentrations which destroyed surrounding bone (bone resorption). Accordingly, endosseous dental implants must be inserted in tight fitting bony sockets, have small diameter or thin wedge-shaped (blade) designs when implanted in narrow bone ridges, and have smooth, rounded root designs for suitable stress distribution. Given these design and implant considerations, bone is more likely to closely appose and support (ankylose) the root structure of an implant.

Most recently problems at the gingival tissue/implant interface have been addressed. In the human, natural teeth and gingival tissue seal where teeth pass through the gingival tissue. This area of sealing is known as the pergingival site. At the pergingival site, gingival connective tissue, and in particular gingival epithelium (the protective layer of cells on the surface of gingiva), join with the surface layer of the tooth, thus isolating the underlying soft and bony tissues from the oral environment. In contrast, prosthetic dental implants currently in use do not seal where they pass through the gingival tissue and consequently leave underlying tissues susceptible to foreign materials, including bacteria. The American Dental Association states that one of the fundamental problems associated with implant design has been ". . . developing an interlocking between the gingival and mucosal tissues and the implant to prevent bacteria penetration and infection in sites where the implant extends into the oral cavity" (American Dental Association, *Dentist's Desk Reference: Materials, Instruments and Equipment,* 1981, p. 149).

The pathological failure of conventional implants at the pergingival site is characterized by a progression of events. After implantation, cellular elements associated with normal tissue swelling and healing deposit a biological fibrous capsule around the implant. Grossly, and in some cases microscopically, the gingival tissue may appear closely adapted to the implant, but with time an epithelial-lined pocket may form between the implant and surrounding gingival tissue. This pocket is evidence of gingival epithelium growing apically (toward the root) along the implant/tissue interface—a phenomenon known as epithelial invagination. Because gingival tissue is not strongly attached to the surfaces of the conventional implant, and because bacteria and normal mechanical forces in the mouth disrupt any close adaptations which might exist between gingival tissue and the implant, a gap is formed along which the epithelium proliferates. The fibrous capsule around the conventional implant is not protected by overlying epithelium and is readily infected. As bacteria break down the fibrous capsule, the pocket extends apically along the implant/gingival tissue interface until it reaches bone where further infection and bone destruction require removal of the implant.

Previous attempts have been made to obtain bacterial seals around pergingival implants. In general, these attempts have consisted of texturing implant surfaces or providing porous coatings at the implant/gingival tissue interface. The resulting devices have either not provided for an interlocking between gingival tissue and the implant or merely slowed the pathological progression of epithelial invagination and implant infection.

The pergingival portions of the conventional carbon and polymethylmethacrylate implants of the prior art have been textured in an attempt to encourage ingrowth of gingival tissue and thus avoid infection. However, porous carbon surfaces have been shown to encourage fibrous capsule formation as described above (Hottel, T. L., and Gibbons, D. F., "The effect of change of surface microstructure of carbon oral implants on gingival surfaces," *J Oral Maxillofac Surg,* 40:647–650, 1982). Porous polymethylmethacrylate implants are subject to epithelial invagination and fracture under forces of mastication (Peterson, L. J.; Perimel, B. M.; McKinney, R. V. Jr., et al: "Clinical radiographical and histological evaluation of porous rooted polymethylmethacrylate dental implants," *J Dent Res,* pp. 493 and 495 Jan. 1979). Polymethylmethacrylate has also been found to be toxic to oral tissue (Garcia, D. A.: "The biocompatibility of dental implant materials measured in an animal model", *J Dent Res*, 60(1):44-9 Jan. 1981).

Another attempt to prevent bacterial invasion has been to incorporate coatings on the pergingival portion of the implant to act as bacterial barriers. One design utilizes nonporous polymers such as tetrafluoroethylene. Nonporous polymers will not provide for the ingrowth and attachment of gingival tissue and are, therefore, subject to the fibrous encapsulation and epithelial invagination of other conventional dental implants.

Other designs have suggested the broad use of fibrous materials, in particular Dacron ® or Proplast ®, at the gingival interface (®Dacron is a registered trademark of E. I. du Pont de Nemours Co., Inc. and ®Proplast is a registered trademark of Dow Corning). However, the unspecified use of fibrous materials does not guarantee a bacterial seal. Previous studies have demonstrated that Proplast ®-coated dental implants encapsulate with fibrous tissue and are prone to epithelial invagination (Svare, C. W.; Glick, P. L.; LaVelle: et al: "A one year study of 'Proplast' coated endosseous implants in primates," *IADR Abstracts*, B196, 1976).

SUMMARY OF THE INVENTION

The present invention overcomes the problems and disadvantages of the prior art by providing a dental implant which provides for an interlocking between the gingival tissue and the gingival interface portion of the dental implant preventing bacterial penetration and infection where the implant extends into the oral cavity.

Additional objects and advantages of the invention will be set forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purposes of the invention, as embodied and broadly described herein, the invention is a dental implant device comprised of a root structure made of a biocompatible, mechanically suitable prosthetic material, a cervical segment connected to and projecting above the root structure, and a gingival interface. The cervical segment is made of a biocompatible, nonporous material and extends above the gingival epithelium tissue and has smooth surfaces. The root structure and the cervical segment are connected to form a member. The gingival interface is formed of expanded polytetrafluoroethylene having a porous microstructure for the ingrowth of connective tissue. The gingival interface is attached to the member adjacent to and preferably at the juncture of the root structure and the cervical segment. The gingival interface forms a border around the apical end of the cervical segment that permits ingrowth of gingival tissue and the formation of an effective bacterial seal adjacent to the apical end of the cervical segment.

It is to be understood that both the foregoing general description and the following detailed description are exemplary and explanatory only and are not restrictive of the invention, as claimed.

The accompanying drawings, which are incorporated in and constitute a part of the specification, illustrate three exemplary embodiments of the invention and, together with the description, serve to explain the principles of the invention.

BRIEF DESCRIPTION OF THE DRAWINGS

FIG. 5 is a three dimensional view of uniaxially expanded polytetrafluoroethylene.

DETAILED DESCRIPTION OF THE PREFERRED EMBODIMENTS

Reference will now be made in detail to the present preferred embodiments of the invention, examples of which are illustrated in the accompanying drawings.

The root structure of the invention can be made from any number of porous or non-porous biocompatible and mechanically suitable materials. Metals include, but are not limited to, titanium and titanium alloys, chromium alloys, tantalum and stainless steels. Aluminum oxide is a suitable ceramic. Any combination of these materials could be utilized. The present preferred embodiment of the invention comprises a pure titanium and/or titanium alloy root structure.

Figure 1:
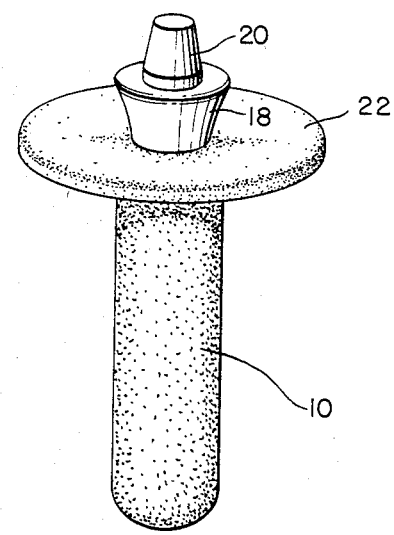
FIG. 1 is a three dimensional view of a first preferred embodiment of the invention.

As shown in FIG. 1, the root structure for an endosseous implant, represented generally by the numeral 10, is designed to have no sharp edges or undercuts which might cause stress concentrations in the surrounding bone after implantation. The root structure may or may not be hollow. If the root structure is not hollow, the inner area of the root structure may be comprised of a porous or a solid stem. The inner portion of the root structure, whether porous or solid, is comprised of any of the forementioned biocompatible and mechanically suitable materials. Possible shapes for the root structure include, but are not limited to, cylinders, hollow cylinders, blades, wedges and cones. Apertures may exist in the root structure to further promote the ingrowth of bony tissue.

If the root structure is not porous, the bone should grow so that the root becomes ankylosed in the jaw bone.

Figure 2:
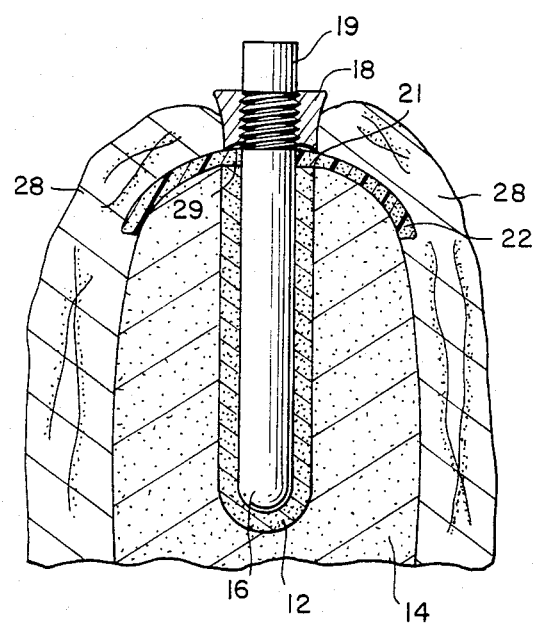
FIG. 2 is a buccal-lingual (from cheek to tongue) cross sectional view of the first preferred embodiment of FIG. 1 when implanted in oral tissue.

Preferably, the outer surface of the root structure is porous. The porous surface 12 in FIG. 2 provides for the ingrowth of bony tissue and secures and supports the root in the jaw bone. FIG. 2 illustrates the first preferred embodiment of the invention implanted into a jawbone 14. A porous coating, if present, may be made of any of the biocompatible materials of the root structure. The porous surface may also be made of coatings including, but not limited to, ceramics such as hydroxylapatite; polymers such as polyethylene, polypropylene, polysulfone or polyurethane; or carbon compositions. Pores should interconnect with one another and should have an average pore diameter of about 50 to 500 microns, preferably about 100 to 300 microns. A porous coating, if present on a solid stem, may be from about 0.1 to 2 mm thick. Preferably, the porous coating is at least about 0.5 mm thick.

The porous surface on the root may be achieved by, among others, a sintering or etching process. The porous coating on the three preferred embodiments can be achieved using a sintering process. In preparing the porous coating, chemically pure titanium particles are sintered around a central, solid, rod shaped core of Ti6Al4V alloy. The sintering process occurs at a temperature near the melting point of titanium in a neutral environment.

The root structure for an endosseous implant, if cylindrical, may be from 5 to 16 mm long. Preferably, the cylindrical root structure is 9 mm long. A wedge or blade-shaped root structure may be from 5 to 16 mm long. Preferably, a wedge or blade-shaped root structure is 9 mm long.

The cylindrical root structure is from 2 to 7 mm in diameter. Preferably, a cylindrical root structure is 4 mm in diameter. A blade-shaped root structure is from 0.5 to 7 mm wide. Preferably, a blade-shaped root structure is 1.25 mm wide. A wedge-shaped root structure is from 7 to 1 mm wide at its broadest point and from 4 to 0.5 mm wide at its narrowest point. Preferably a wedge-shaped root structure is 1.5 mm wide at its broadest point and 1 mm wide at its narrowest point.

Figure 3A:
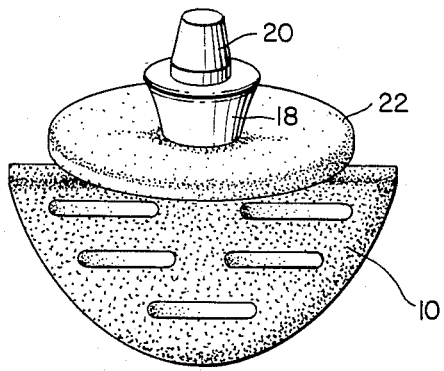
FIG. 3A is a three dimensional view of a second preferred embodiment.
Figure 3B:
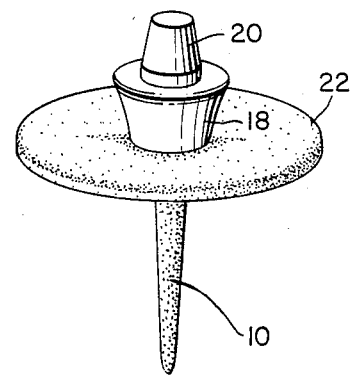
FIG. 3B is a side view of the second preferred embodiment of FIG. 3A.
Figure 4A:
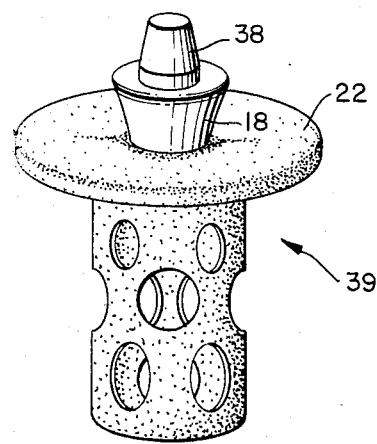
FIG. 4A is a three dimensional view of a third preferred embodiment of the invention.
Figure 4B:
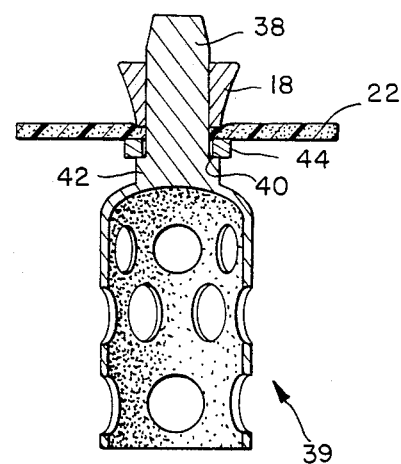
FIG. 4B is a cross sectional view of the third preferred embodiment of FIG. 4A.

In one preferred embodiment, the root structure has a solid inner stem and a porous surface in a cylindrical shape. The solid inner stem 16 is shown in FIG. 2. FIG. 1 illustrates the implant with a cylindrical root structure 10. The second preferred embodiment is illustrated in FIGS. 3A and 3B wherein root structure 10 is blade shaped with apertures for the ingrowth of bony tissue. The third preferred embodiment is illustrated in FIGS. 4A and 4B. In this embodiment, root structure 39 is a hollow cylinder with an open end opposite the gingival interface.

The cervical segment of the invention serves as an attachment for artificial teeth or other dental prostheses. The cervical segment 18 in FIG. 1 is illustrative of the preferred embodiment. The cervical segment of the invention is nonporous, has smooth surfaces, and is constructed from a biocompatible material. The smooth surfaces are necessary so as not to inhibit the growth of gingival epithelium towards the gingival interface, a phenomenon known as "turning down". Porous or rough surfaces are not suitable as they may trap bacteria and/or inhibit the extension of the gingival epithelium to the expanded PTFE gingival interface. The root materials listed above that provide a smooth and nonporous surface would also be suitable for the cervical segment. Additional biocompatible materials that are suitable for the cervical segment include, but are not limited to, polyurethanes, polysulfones, polycarboxylates, perfluorinated polymers, such as polytetrafluoroethylene and fluorinated ethylene propylene, polyacrylics, silicone, etc.

The profile of the cervical segment desirably narrows apically (as it passes from the oral cavity to the gingival interface). This narrowing causes the horizontal cross section of the cervical segment to decrease as it approaches the gingival interface 22 as viewed in FIG. 2. After the invention has been implanted and artificial teeth affixed, this narrowing (as with natural teeth) may protect the point of epithelial attachment to the gingival interface by deflecting food away from the attachment point. The cervical segment is preferably smooth, non-porous titanium and narrows as it approaches the gingival interface. The cervical segment tapers curvilinearly. In the preferred embodiments, the cervical segment 18 as viewed in FIG. 2, tapers apically from an outer diameter at its upper surface of about 5 mm to an outer diameter at its lower surface of about 4 mm. A coping 20 as illustrated in FIGS. 3, 3A, and 3B, may be attached to or be an extension of the cervical segment 18, or a post extending up from the root structure. The coping 20 extends further into the oral cavity and may serve as an attachment for dental prostheses and artifical teeth.

The gingival interface 22 is located adjacent to and preferably at the juncture of the root structure and the cervical segment as shown in FIG. 1. The gingival interface is comprised of expanded polytetrafluoroethylene (PTFE). The structure of the expanded PTFE provides for rapid connective tissue ingrowth and vascularization while being resistant to crushing. In addition, the expanded PTFE allows for growth of bony tissue into the gingival interface. U.S. Pat. Nos. 3,953,566 and 4,187,390, the disclosures of which are incorporated herein by reference, teach the methods for producing expanded PTFE and characterize its porous structure.

Expanded PTFE is an extremely inert and biocompatible material with a history of medical implant use. The porous structure of expanded PTFE is further illustrated by FIG. 5. The microstructure of expanded PTFE is a three-dimensional matrix of nodes 24 connected by fibrils 26.

The pore size of expanded PTFE can be characterized by determining the bubble point (BP) of the material. BP is measured according to the American Society for Testing and Materials Standard F316-80 using methanol.

The density of expanded PTFE determines the amount of void space in the material which may become ingrown with connective tissue. The density of expanded PTFE is the ratio of the mass of a given sample of expanded PTFE to its volume.

The fibril length of expanded PTFE is defined herein as the average of ten measurements between nodes connected by fibrils in the direction of expansion. Although FIG. 5 illustrates material expanded in one direction only, PTFE expanded in more than one direction is thought to be equally applicable to the invention. In order to measure the average fibril length of expanded PTFE, two parallel lines are drawn across a photomicrograph of about 40 to 50 times magnification of the surface of the material so as to divide the photograph into three equal areas. If the material has been uniaxially expanded, these lines are drawn in the direction of expansion (i.e. direction of orientation of fibrils). Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the righthand side of the photograph. If the material is expanded in more than one direction, the lines are drawn and fibril lengths measured as above, except when a node is not attached by fibrils to a node intersecting the drawn line. In this case, the fibril length from the node to a node which creates the least angle with the drawn line is measured along the fibrils axial orientation. The ten measurements obtained by this method are averaged to obtain the average fibril length of the material.

Average fibril lengths greater than about 60 microns, preferably in the range of about 100 to 150 microns, methanol bubble points of less than about 3.5 psi, and preferably of about 0.9 to 0.1 psi, and densities less than about 1 g/cc and preferably about 0.3 to 0.1 g/cc enhance connective tissue ingrowth.

Desirably, and as illustrated in FIG. 5, a number of nodes 24 pass through the wall thickness of the expanded PTFE to provide channels for tissue ingrowth and a wall resistant to crushing. Expanded PTFE without nodes passing through its wall thickness is more easily crushed by forces of mastication, thereby decreasing the pore size, increasing the density, and compromising ingrowth. Preferably, a majority of the nodes extend across the thickness dimension of the wall. In the preferred embodiments an expanded PTFE gingival interface with a wall thickness of appoximately 1 millimeter is used.

The expanded PTFE gingival interface may be of several configurations and may be attached to the cervical segment and/or root structure at the juncture of the root structure and cervical segment by any suitable means. In one embodiment, as depicted in FIG. 2, the gingival interface 22 is a circular disc of expanded PTFE with a hole in its center fit over a post 19 protruding from the portion of the root structure having a coating 12. The top surface of coating 12 forms a circumferential ledge 21 around the bottom of post 19. Gingival interface 22 is then pressed between ledge 21 and a cervical segment 18 which is screwed onto the post but may be attached by any suitable means. A medical grade adhesive which penetrates the expanded PTFE around the post and out to a diameter no greater than the cervical segment diameter where it meets the gingival interface adheres the disc of expanded PTFE to the junction of the cervical segment and the root.

An expanded PTFE gingival interface may also be applied as a concentric cylinder around the junction of the root and cervical segment and may or may not protrude out from the surface of the implant. Such a concentric cylinder could also be combined with a disc of expanded PTFE as described above.

The implant may be assembled as above from individual components of a root and a cervical segment with a gingival interface compressed and/or adhered between the root and the cervical segment. The implant may also be assembled from a one-piece root/cervical segment to which an expanded PTFE gingival interface is adhered.

The gingival interface may also be attached to the implant structure by molding the cervical segment from a suitable, biocompatible polymer. The cervical segment can be molded onto the root structure with the expanded PTFE gingival interface in place. As the polymer forms the cervical segment, it also penetrates the porous structure of the expanded PTFE thereby adhering it to the cervical segment/root junction.

When the invention is implanted, standard dental procedures are used. For example, an incision may be made through the gingiva along the crest of the jawbone so that two gingival flaps 28 may be laid back exposing the underlying bone tissue. Prior to forming the flaps a trephined hole in the gingiva may also be made to fit the cervical segment where it protrudes through the gingiva into the oral cavity. If the implant is to be inserted in the jaw bone (an endosseous implant) and not lie on the jaw bone (subperiosteal implant), a socket can be prepared in the bone using conventional dental drills and burs. The socket should be formed to closely appose the implant root and thus avoid the formation of fibrous tissue around the root. When the implant is inserted in the socket, the gingival interface should lie on the crest of the jaw bone or within the gingival tissue. A gingival interface of expanded PTFE which protrudes from the body of the implant, such as the interface 22 in FIG. 2, is flexible and conforms easily to the curvature of the jaw bone crest. After the implant is inserted in or on the jaw bone, the gingival tissue flaps 28 may be brought up and sutured around the cervical segment 18 so that the gingival tissue flaps 28 take the position shown in FIG. 2.

After implantation, the cervical segment protrudes through the gingival tissue into the oral cavity, and the expanded PTFE gingival interface lies in or against the connective tissue of the gingiva. The expanded PTFE fills readily with vascularized connective tissue. Gingival epithelium proliferates apically along the cervical segment until it reaches the expanded PTFE. The epithelium appears to halt its apical growth and attach to the connective tissue in the expanded PTFE gingival interface near the junction of the gingival interface with the root and cervical segment. The attachment of gingival epithelium to connective tissue in the expanded PTFE gingival interface creates a bacterial seal surrounding the implant similar to the epithelial attachment and bacterial seal surrounding natural teeth at the cervical line. The invention inhibits bacterial penetration and prevents the epithelial invagingation and resultant infection of prior art dental implants.

The invention will be further clarified by the following examples, which are intended to be purely exemplary of the invention.

EXAMPLE 1

Dental implants similar to that illustrated in FIG. 2 were produced and implanted in dogs. The dog was chosen as an animal model because dogs have been used by other investigators to test the safety and effectiveness of dental implants intended for human application (Weiss, M. B. and Rostoker, W., "Development of a new endosseous dental implant", Part I: Animal Studies, *Maxillofacial Prosthetics* 46:646, 1981; McKinney, R. W. and Koth, D. L., "The single-crystal sapphire endosteal dental implant: Material characteristics and 18 month experimental animal trials", *Maxillofacial Prosthetics* 47:69, 1982; Brunski, J. B., et al, "The influence of functional use of endosseous dental implants on the tissue-implant interface II clinical aspects", *J Dent Res* 58(1), Oct. 1979; Weinstein, A. M., et al, "An evaluation of ion-textured aluminum oxide dental implants", *J Biomed Mat Research* 15 (749–756), 1981).

In order to construct the dental implants, the cervical segments, expanded PTFE gingival interfaces, and root structures were constructed separately and then assembled. The root structures for the implants were constructed by sintering chemically pure titanium particles around a central, solid, rod-shaped core of Ti6Al4V alloy. The particles were sintered to the core near the melting temperature of the titanium in a neutral environment. The rod shaped central core was covered with titanium particles so that the finished root structure was a cylinder with one rounded end. The central rod core extended through the porous metal cylinder end opposite the rounded end. The protruding core was threaded to accept a cervical segment. The porous metal coating on the central core was approximately 1 mm thick and designed to provide interconnecting pores of pore diameter from 100 to 150 microns. The cylinders were approximately 4 mm in diameter and 9 mm long.

The cervical segments were machined from Ti6Al4V alloy. Each segment was mushroom shaped and tapered apically as two blended curves from an outer diameter of 4.8 mm to an outer diameter of 4 mm at the base. The cervical segment was about 4.3 mm in height and was internally threaded to accept the central core rod of the root structure. The cervical segment bases were concave 29 so that medical grade adhesive could be deposited in the base to bond the expanded PTFE gingival interface to the cervical segment.

The expanded PTFE gingival interface was made according to the art described in U.S. Pat. Nos. 4,187,390 and 3,953,566 as follows: A dispersion of PTFE resin in a liquid lubricant was extruded into a tubular form. The extruded form was dried for approximately 24 hours at 295° C., which also removed the lubricant. The form was then stretched at a constant velocity along the central axis of the tube at a rate of about 55 to 60% per second until it was approximately 8.5 times its original length, where rate was defined as $(l_f - l_i) \times 100\%$, and $l_f$=final length, $l_i$=initial length, and $l_i(t)$ t=total time of expansion. Subsequent to stretching, the tube was restrained longitudinally and heat treated at about 375° C. for approximately 40 seconds. This expanded PTFE tube was slit longitudinally through its wall and laid flat. The final PTFE material had an average fibril length of approximately 100 to 150 microns, a methanol BP of about 0.9 to 0.1 psi, a density of about 0.3 to 0.1 g/cc, and a majority of nodes passing through its wall thickness. Approximately 9.5 mm diameter discs were cut from the expanded PTFE. A hole slightly smaller than the central core rod 16 of the root was punched in the center of the discs, and the central core rods of the root structures were then inserted through the holes in the discs. Medical grade silicone adhesive, obtained from Dow-Corning Corporation, was deposited in the concave base 29 of the cervical segments. The cervical segment was screwed down over the rod protruding from the porous root structure until the expanded PTFE gingival interface was slightly crushed between the cervical segment and the root structure. When the adhesive had cured, the devices were ready for sterilization.

Implants were sterilized in preparation for insertion into the jaw bones of dogs. The second and fourth premolars of the dogs were extracted and the extraction sites allowed to heal for approximately three months. Small holes and midline crestal incisions were created in the gingiva as described in Example 2. Cylindrical holes sized to fit the implant root structure were drilled in the exposed jaw bone using conventional dental burs and drills. The implant root structures were then fit tightly in the cylindrical holes so that the expanded PTFE gingival interface rested on the ridge crest. The gingival interfaces were laid over the ridge and the gingival flaps brought up and sutured around the cervical segments. Seven implants were inserted according to this method. After implantation periods ranging from one month to five months, the gingival tissue surrounding the implants appeared healthy and normal with no evidence of infection. Probing the gingival tissue around the cervical segments revealed that the gingival epithelium had apparently turned down and extended to the expanded PTFE gingival interface. Radiographs revealed that bone had closely apposed the implant root structure. In all but one device, which had been implanted in a ridge too thin to accommodate the diameter of the root, there was no evidence of epithelial invagination, bone loss, or infection.

EXAMPLE 2

To test the bacterial seal surrounding pergingival implants, sixteen implants were constructed and implanted through the gingival tissue in dogs. The implants consisted only of cervical segments attached to gingival interfaces of expanded PTFE, because only the bacterial seal surrounding the implants and not the roots was to be tested. Cervical segments were molded from a medical grade silicone elastomer and were mushroom shaped having circular perimeters and profiles which narrowed to a diameter of approximately 3.5 mm at the apical end. The apical bases of the cervical segments were adhered to the center of round flat discs of expanded PTFE, as described in Example 1, using a medical grade silicone adhesive obtained from Dow-Corning Corp. The expanded PTFE discs were approximately 11 mm in diameter and had a 1 mm wall thickness. The expanded PTFE had a majority of nodes passing through its wall thickness, an average fibril length of about 100 to 150 microns, methanol BP of about 0.9 to 0.1 psi, and density of about 0.3 to 0.1 g/cc.

The second and fourth mandibular premolars were extracted from the animals prior to implantation to create four sites in each animal at which to test the implants. After bone and gingival tissue had healed at the extraction sites, small holes approximating the diameter of the cervical segments and midline incisions through the holes were created through the gingival tissue using a trephine and scalpel along the crest of the jawbone at all four sites. Gingival flaps were then laid back to expose the underlying bone ridges. One implant was laid on the bone ridge in each site so that the expanded PTFE gingival interfaces saddled the bone ridge and the cervical segments were situated at the crest of the ridge. The gingival flaps were then returned to their original positions so that the expanded PTFE gingival interfaces were covered with gingival tissue and the cervical segments protruded through the trephine holes into the oral environment. The midline incisions were then sutured closed on either side of the implants.

Sixteen implants were retrieved one month to three months after implantation to determine grossly and histologically whether bacterial seals had been created. Grossly, the gingival tissue around all implants appeared healthy and normal with no evidence of infection (i.e., there was no reddening or inflmmation). Microscopically, at one and three month periods, the expanded PTFE gingival interface had filled with healthy, vascularized connective tissue. Gingival epithelium was found in various stages of turning down next to the cervical segment and had in many cases grown apically to the expanded PTFE gingival interface and attached to the connective tissue within the gingival interface. The attachment was near or at the junction of the expanded PTFE gingival interface and the cervical segments. There was no evidence of infection in any of the implants.

EXAMPLE 3

Conventional dental implants were modified to produce implants similar to that illustrated in FIGS. 4A and 4B. The pergingival portion of conventional titanium hollow cylinder implants, sold under the mark "Colstram-d" by COLMED LTD., was modified with a cervical segment and expanded PTFE gingival interface. The pergingival post 38 of each conventional implant, generally represented by the numeral 39, was machined so that a ledge 40 was created around each post approximately 1.5 mm above the shoulder 42 of the hollow cylinder root. A titanium washer 44 with an outer diameter of 4.0 mm and an inner diameter slightly larger than the diameter of the post after machining was placed on the post and seated on shoulder 42. An expanded PTFE gingival interface 22 and a cervical segment 18, as described in Example 1, were also placed concentrically on the post and positioned so that the gingival interface was slightly crushed between the washer and the cervical segment. Medical grade silicone adhesive was also utilized as described in Example 2. A titanium screw (not shown) extending through cervical segment 18 and into post 38 attached cervical segment 18 to conventional implant 39 and secured the gingival interface 22 between the root structure (washer 44 and the hollow basket lower portion of implant 39) and cervical segment 18.

Two hollow cylinder implants modified with an expanded PTFE gingival interface and cervical segment were placed in the mandibles of dogs according to the methods described in Example 1. Hollow cylindrical holes were created in the jaw bone of the dogs with trephine drills to accommodate the hollow cylinder root structure of the implants. Eight months after the implants had been placed in the dogs, gingival tissue surrounding the implants appeared normal and healthy. In all cases there was no evidence of epithelial invagination, bone loss, or infection.

It will be apparent to those skilled in the art that various modifications and variations can be made in the dental implant of the present invention and in the construction of this implant without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A dental implant device comprising:
   a. a root structure made of a biocompatible, mechanically suitable prosthetic material;
   b. a cervical segment connected to and projecting above said root structure, said cervical segment made of a biocompatible, nonporous material and extending above the gingival epithelial tissue and having smooth surfaces, said root structure and said cervical segment forming a member; and
   c. a gingival interface comprising a porous polytetrafluoroethylene member having a pair of spaced surfaces that define a wall thickness for the polytetrafluoroethylene member with both spaced surfaces extending outwardly from the periphery of the root structure and the cervical segment to permit tissue ingrowth into each of said spaced surfaces.

2. The dental implant of claim 1, wherein said expanded polytetrafluoroethylene gingival interface has an average fibril length greater than about 60 microns and a density of less than about 1 g/cc.

3. The dental implant of claim 1, wherein said expanded polytetrafluoroethylene gingival interface is a circular disc attached to and surrounding the junction of said root structure and said cervical segment at the apical end of said cervical segment.

4. The dental implant of claim 1, wherein said expanded polytetrafluoroethylene gingival interface is a concentric cylinder attached to and surrounding the junction of said root structure and said cervical segment at the apical end of said cervical segment.

5. The dental implant of claim 1, wherein said cervical segment is formed from a biocompatible, nonporous material which penetrates the porous structure of said expanded polytetrafluoroethylene gingival interface and adheres said expanded polytetrafluoroethylene gingival interface to the junction of said root structure and said cervical segment at the apical end of said cervical segment.

6. The dental implant of claim 1, wherein said cervical segment's perimeter is continuously curved and its cross section decreases apically, with the apical end contacting said expanded polytetrafluoroethylene gingival interface.

7. The dental implant of claim 1, wherein said root structure is a solid cylinder with a rounded apical end.

8. The dental implant of claim 1, wherein said root structure is a hollow cylinder.

9. The dental implant of claim 1, wherein said root structure is a blade.

10. The dental implant of claim 2, wherein said expanded polytetrafluoroethylene gingival interface has a methanol bubble point of less than about 3.5 psi and a density less than about 0.6 g/cc and a majority of nodes passing through the wall thickness of said expanded polytetrafluoroethylene.

11. The dental implant of claim 7, wherein said root structure has a porous surface.

12. The dental implant of claim 7, wherein said root structure contains apertures to promote bony ingrowth.

13. The dental implant of claim 7, wherein said root structure has a porous surface of sintered titanium.

14. The dental implant of claim 8, wherein said root structure has a porous surface.

15. The dental implant of claim 8, wherein said root structure contains apertures to promote bony ingrowth.

16. The dental implant of claim 8, wherein said root structure has a porous surface of sintered titanium.

17. The dental implant of claim 9, wherein said root structure has a porous surface.

18. The dental implant of claim 9, wherein said root structure contains apertures to promote bony ingrowth.

19. The dental implant of claim 9, wherein said root structure has a porous surface of sintered titanium.

20. The dental implant of claim 10, wherein said expanded polytetrafluoroethylene gingival interface has an average fibril length of about 100 to 150 microns and a methanol bubble point of about 0.9 to 0.1 psi and a density of about 0.3 to 0.1 g/cc.

21. The dental implant of claim 11, wherein said porous surface has an average pore diameter of 100 to 300 microns.

22. The dental implant of claim 14, wherein said porous surface has an average pore diameter of 100 to 300 microns.

23. The dental implant of claim 17, wherein said porous surface has an average pore diameter of 100 to 300 microns.

24. The dental implant of claim 1 wherein a majority of nodes pass through said wall thickness.

* * * * *